US011426177B2

(12) United States Patent
Congdon et al.

(10) Patent No.: US 11,426,177 B2
(45) Date of Patent: Aug. 30, 2022

(54) HEMOSTASIS CLIP DEPLOYMENT

(71) Applicant: Boston Scientific Scimed, Inc., Maple Grove, MN (US)

(72) Inventors: Daniel Congdon, Hudson, MA (US); Laurie A. Lehtinen, Boylston, MA (US); Alex Roberts, Newton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 275 days.

(21) Appl. No.: 16/861,135

(22) Filed: Apr. 28, 2020

(65) Prior Publication Data
US 2020/0375602 A1 Dec. 3, 2020

Related U.S. Application Data

(60) Provisional application No. 62/853,334, filed on May 28, 2019.

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 2017/0034* (2013.01);
(Continued)

(58) Field of Classification Search
CPC .. A61B 2017/0034; A61B 2017/12004; A61B 17/122; A61B 17/1227; A61B 17/128; A61B 17/1285
See application file for complete search history.

(56) References Cited

U.S. PATENT DOCUMENTS 6,193,732 B1 * 2/2001 Frantzen ............. A61B 17/128
606/151
8,152,824 B2 * 4/2012 Kimura ............. A61B 17/1285
24/537

(Continued)

FOREIGN PATENT DOCUMENTS

| CN | 108969050 | 12/2018 |
| CN | 109394291 | 3/2019 |
| WO | 2019/147437 | 8/2019 |

*Primary Examiner* — Ryan J. Severson
(74) *Attorney, Agent, or Firm* — Fay Kaplun & Marcin, LLP

(57) ABSTRACT

A device includes a clip including a capsule and a pair of clip arms, proximal ends of which are slidably received within a channel of the capsule to move the clip arms between an open configuration and a closed configuration. The clip arms are aligned relative to one another via a pin received within openings extending through proximal ends of the clip arms. A proximal portion includes a flexible shaft extending from a proximal end to a distal end including a bushing releasably coupled to the capsule. A control member extends longitudinally through the flexible shaft from a proximal end to a distal end releasably coupled to the proximal ends of the clip aims, the distal end of the control member including a pair of holding jaws, each of which include a pair of fingers extending about the pin along opposing sides thereof to grip the pin therebetween.

20 Claims, 3 Drawing Sheets

(51) Int. Cl.
  *A61B 17/00* (2006.01)
  *A61B 17/12* (2006.01)
(52) U.S. Cl.
  CPC ............ *A61B 2017/00818* (2013.01); *A61B 2017/12004* (2013.01)

(56) References Cited

U.S. PATENT DOCUMENTS

| | | | | |
|---|---|---|---|---|
| 8,157,824 B2* | 4/2012 | Kimura | ............ | A61B 17/1285 24/537 |
| 8,348,964 B2* | 1/2013 | Kimura | ............ | A61B 17/1222 606/157 |
| 8,444,660 B2* | 5/2013 | Adams | ............ | A61B 17/122 606/157 |
| 8,663,247 B2* | 3/2014 | Menn | ............ | A61B 17/1285 606/142 |
| 8,685,048 B2* | 4/2014 | Adams | ............ | A61B 17/1227 606/157 |
| 8,709,027 B2* | 4/2014 | Adams | ............ | A61B 17/1285 606/142 |
| 9,005,219 B2* | 4/2015 | Cohen | ............ | A61B 17/1227 606/151 |
| 9,072,520 B2* | 7/2015 | Terada | ............ | A61B 17/1222 |
| 9,271,731 B2* | 3/2016 | Adams | ............ | A61B 17/083 |
| 9,332,988 B2* | 5/2016 | Adams | ............ | A61B 17/1285 |
| 9,931,124 B2* | 4/2018 | Gokharu | ............ | A61B 17/1285 |
| 9,974,532 B2* | 5/2018 | Baas | ............ | A61B 17/083 |
| 10,143,479 B2* | 12/2018 | Adams | ............ | A61B 17/1285 |
| 10,172,623 B2* | 1/2019 | Adams | ............ | A61B 17/1227 |
| 10,172,624 B2* | 1/2019 | Adams | ............ | A61B 17/083 |
| 10,765,435 B2* | 9/2020 | Gokharu | ............ | A61B 17/1222 |
| 10,820,904 B2* | 11/2020 | Ryan | ............ | A61B 17/10 |
| 10,905,434 B2* | 2/2021 | Estevez | ............ | A61B 17/0057 |
| 10,952,742 B2* | 3/2021 | Lehtinen | ............ | A61B 90/03 |
| 10,952,743 B2* | 3/2021 | Adams | ............ | A61B 17/1227 |
| 11,071,552 B2* | 7/2021 | Saenz Villalobos | ............ | A61B 17/1227 |
| 11,076,862 B2* | 8/2021 | Uesaka | ............ | A61B 17/1222 |
| 11,083,465 B2* | 8/2021 | Ryan | ............ | A61B 17/1227 |
| 11,129,623 B2* | 9/2021 | Saenz Villalobos | ............ | A61B 17/083 |
| 11,141,166 B2* | 10/2021 | Itoh | ............ | A61B 17/1285 |
| 11,141,167 B2* | 10/2021 | Tsuchiya | ............ | A61B 17/1285 |
| 11,234,686 B2* | 2/2022 | Congdon | ............ | A61B 17/0057 |
| 11,259,815 B2* | 3/2022 | Han | ............ | A61B 17/29 |
| 2005/0107809 A1* | 5/2005 | Litscher | ............ | A61B 17/122 606/142 |
| 2011/0046651 A1* | 2/2011 | Cohen | ............ | A61B 17/1227 606/157 |
| 2015/0190136 A1* | 7/2015 | Cohen | ............ | A61B 17/1227 606/143 |
| 2016/0242778 A1* | 8/2016 | Xu | ............ | A61B 17/08 |
| 2016/0367258 A1 | 12/2016 | Jin et al. | | |
| 2018/0085122 A1* | 3/2018 | Ryan | ............ | A61B 17/1227 |
| 2019/0159783 A1* | 5/2019 | Lehtinen | ............ | A61B 17/122 |
| 2019/0223875 A1* | 7/2019 | Saenz Villalobos | ............ | A61B 17/1285 |
| 2019/0231353 A1* | 8/2019 | Saenz Villalobos | ............ | A61B 17/083 |
| 2020/0093496 A1* | 3/2020 | Ryan | ............ | A61B 17/1285 |
| 2020/0205836 A1* | 7/2020 | Uesaka | ............ | A61B 17/1227 |
| 2020/0375583 A1* | 12/2020 | Congdon | ............ | A61B 17/1285 |
| 2020/0375602 A1* | 12/2020 | Congdon | ............ | A61B 17/1227 |
| 2020/0397437 A1* | 12/2020 | Congdon | ............ | A61B 17/1227 |

\* cited by examiner

HEMOSTASIS CLIP DEPLOYMENT

PRIORITY CLAIM

The preset disclosure claims priority to U.S. Provisional Patent Application Ser. No. 62/853,334 filed May 28, 2019; the disclosure of which is incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract or may require closure of the GI tract wall as part of the procedure. Hemostasis clips may be used for endoscopic hemostasis of, for example, mucosal/sub-mucosal defects, bleeding ulcers, arteries, polyps, diverticula, along with closure of luminal tract perforations. Depending on the size of the defect, multiple clips may be required.

SUMMARY

The present disclosure relates to a clipping device, comprising a clip including a capsule extending longitudinally from a proximal end to a distal end and including a channel extending therethrough, and a pair of clip arms, proximal ends of which are slidably received within the channel to move the clip arms between an open configuration, in which distal ends thereof are separated from one another, and a closed configuration, in which the distal end of the clip arms are drawn toward one another. The clip arms are aligned relative to one another via a pin received within openings extending through proximal ends of the clip arms. A proximal portion is configured for insertion of the clip through a working channel of an endoscope, the proximal portion including a flexible shaft extending from a proximal end to a distal end including a bushing releasably coupled to the capsule. A control member extends longitudinally through the flexible shaft from a proximal end to a distal end releasably coupled to the proximal ends of the clip arms to move the clip arms between the open and closed configurations, the distal end of the control member including a pair of holding jaws, each of which include a pair of fingers extending about the pin along opposing sides thereof to grip the pin therebetween.

In one embodiment, the proximal end of the capsule may include tabs biased radially inward to engage a corresponding structure of the bushing.

In one embodiment, the distal end of the control member may include a pair of spacing jaws configured to extend between the proximal ends of the clip arms along opposing sides of the pin. The pair of spacing jaws may be sized and shaped so the pair of spacing jaws move the tabs radially outward as the distal end of the control member is moved proximally past the proximal end of the capsule to deploy the clip from the proximal portion of the device.

In one embodiment, the proximal ends of the clip arms may be biased radially outward.

In one embodiment, the pair of holding jaws may extend over an exterior surface along a proximal end of a corresponding one of the clip arms to constrain the clip arms toward an unlocked configuration in which locking structures at the proximal ends of the clip anus are prevented from engaging corresponding locking features of the capsule.

In one embodiment, the locking structures may include locking tabs extending from proximal ends of the clip arms and the locking features of the capsule may include windows extending laterally through a wall thereof so that, when the proximal ends of the clip are released from the distal end of the control member, the locking tabs are received within the locking windows to lock the clip in the closed configuration.

In one embodiment, the clip arms may be biased toward the open configuration so that the clip arms are constrained toward the closed configuration via an interior surface of the capsule and revert to the biased open configuration when the clip arms are moved distally out relative to the capsule.

In one embodiment, the clip anus may include engaging features configured to engage portion of the capsule such that, when the engaging features engage the capsule, the clip arms are prevented from moving further proximally relative to capsule and the predetermined force is exerted on the distal end of the control member.

The present disclosure relates to a clipping device, comprising a clip including a capsule extending longitudinally from a proximal end to a distal end and including a channel extending therethrough, and a pair of clip arms, proximal ends of which are slidably received within the channel to move the clip arms between an open configuration, in which distal ends thereof are separated from one another, and a closed configuration, in which the distal end of the clip arms are drawn toward one another. A proximal portion is configured for insertion of the clip through a working channel of an endoscope, the proximal portion including a flexible shaft extending from a proximal end to a distal end including a bushing releasably coupled to the capsule. A control member extends through the flexible shaft from a proximal end to a distal end releasably coupled to the proximal ends of the clip arms to move the clip arms between the open and the closed configurations, the distal end including a middle portion received between the proximal ends of the clip arms. A first portion of a pin and a second portion of a pin extend away from opposing surface of the middle portion to be received in openings extending through proximal ends of the clip arms to maintain an alignment of the clip aims relative to one another, the first and second portions being pulled proximally out of the openings of the clip arms and past a proximal edge thereof when a predetermined force is exerted on the clip arms via the distal end.

In one embodiment, each of the first and second portions may include an overhang extending therefrom to extend over a portion of an exterior surface along the proximal end of a corresponding one of the clip anus to constrain outwardly biased proximal ends of the clip arms toward an unlocked configuration, in which proximal ends are constrained toward a middle portion received therebetween so that locking structures along the proximal ends of the clip aims are prevented from engaging corresponding locking features of the capsule.

In one embodiment, each of the clip arms may include a slot extending proximally from the opening to a proximal edge thereof to define two fingers which flex apart from one another to release the pin therefrom, when the predetermined force is exerted on thereon.

In one embodiment, each of the clip arms may include reliefs along longitudinal edges of the clip arm immediately distal of the opening to facilitate flexing of the two fingers away from one another.

In one embodiment, each of the clip arms may include a notch extending along a surface thereof from the opening to a proximal edge thereof so that, when the predetermined force is exerted thereon via the pin, the clips separate along the notch to release the pin from the openings.

In one embodiment, first and second portions of the pin may taper toward a proximal end thereof to split each of the clip arms along the notch.

In one embodiment, the proximal end of the capsule may include tabs biased radially inward to engage a corresponding structure of the bushing, the middle portion being sized and shaped to move the tabs radially outward as the distal end of the control member is moved proximally past the proximal end of the capsule to deploy the clip from the proximal portion of the device.

The present disclosure also relates to a method for treating a target tissue, comprising inserting a clip device through a working channel of an endoscope to a target site within a body until a clip of the clip device extends distally past a distal end of the working channel. The clip device includes a capsule and a pair of clip arms slidably received therein, the pair of clip arms aligned relative to one another via a pin extending through openings extending through proximal ends of the clip arms. The clip device moves between an open configuration, in which distal ends of the clip aims are separated from one another, and a closed configuration, in which the distal ends of the clip aims are drawn toward one another, via a control wire coupled to the clip arms, until a target tissue is received between the distal ends as desired. A distal end of the control wire is coupled to proximal ends of the clip aims via first and second holding jaws, each of which include a pair of fingers extending about the pin along opposing sides thereof to grip the pin therebetween. The clip arms are drawn proximally into the capsule to move the clip toward the closed configuration to grip the target tissue between the clip aims. The clip is deployed from a proximal portion of the clip device by drawing the control member proximally relative to the capsule until a predetermined force is exerted on the distal end of the control wire to spread the fingers apart from one another and release the pin from therebetween.

BRIEF DESCRIPTION

DETAILED DESCRIPTION

Figure 1:
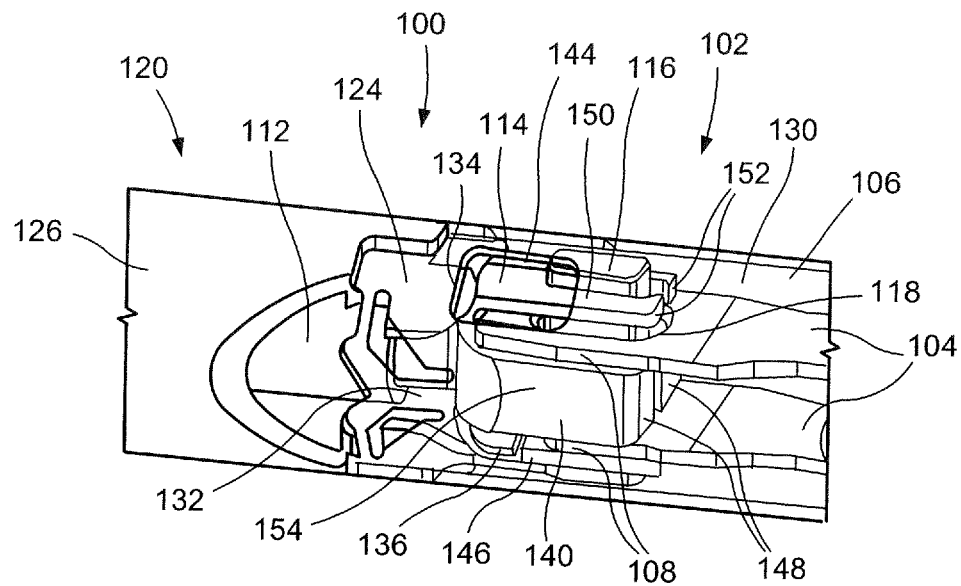
FIG. 1 shows a partially transparent perspective view of a portion of a clipping device according to a first exemplary embodiment of the present disclosure, in a pre-deployed configuration.

The present disclosure may be further understood with reference to the following description and the appended drawings, wherein like elements are referred to with the same reference numerals. The present disclosure is directed to an endoscopic clipping device for treating tissue perforations, defects and/or bleeds. A clipping device may comprise a clip including clip arms, proximal ends of which are slidably received within a capsule to move the clip between an open configuration and a closed configuration to clip a target tissue, as desired. Clip arms may be moved via a control member such as a control wire connected between the proximal end of the clip and a handle of the device that, during use, remains outside the body accessible to a user. In some cases, a shorter deployed clip may be preferred to improve visualization of the target site and to allow better maneuverability when placing multiple clips.

In addition, although shed parts will pass naturally under normal circumstances, some physicians are concerned that, particularly for larger defects, shed parts resulting during and/or after deployment of some current clip designs may become trapped in the defect after closure. Exemplary embodiments of the present disclosure describe a control member having a distal end configured to be directly and releasably coupled to the proximal ends of the clip anus so that, upon deployment of the clip in the body, as will be described in further detail below, the control member separates from the clip leaving no portion of a deployment mechanism extending out of the capsule, thereby reducing a potential length of the deployed clip and/or shed parts of the clip into the body. It will be understood by those of skill in the art that the terms proximal and distal, as used herein, are intended to refer to a direction toward (proximal) and away from (distal) a user of the device.

Figure 2:
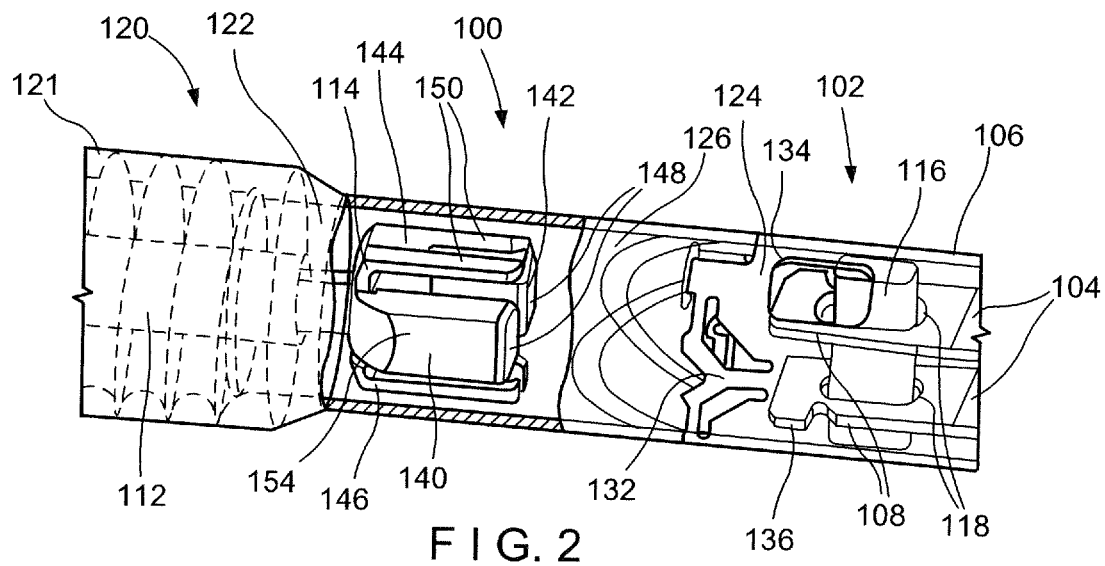
FIG. 2 shows a partially transparent perspective view of the clipping device of FIG. 1, in a deployed configuration.
Figure 3:
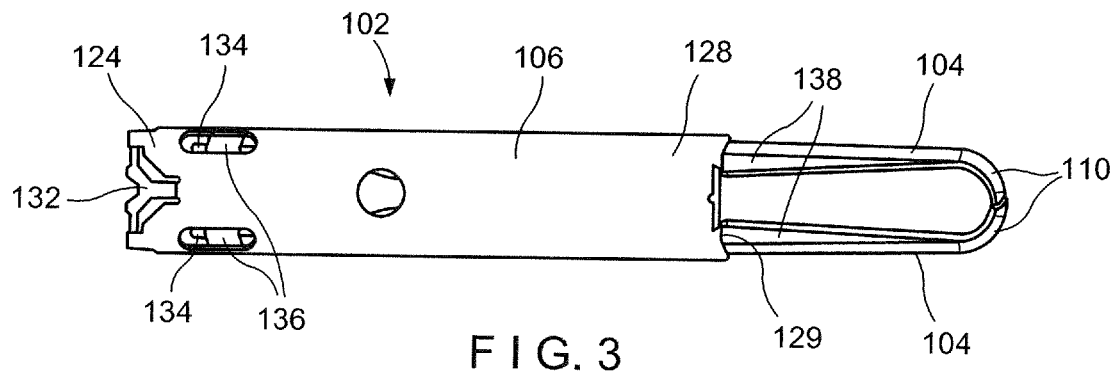
FIG. 3 shows a longitudinal side view of a deployed portion of the clipping device according to FIG. 1.

As shown in FIGS. 1-3, a clipping device 100 for treating tissue defects comprises a clip 102 including a pair of clip arms 104 having proximal ends 108 which are slidably received within a capsule 106 so that the clip 102 may move between an open configuration, in which distal ends 110 of the clip arms 104 are separated from one another, and a closed configuration, in which distal ends 110 are drawn toward one another. The clip arms 104 are movable between the open and the closed configurations via a control member 112, which includes a distal end 114 configured to be directly coupled to the proximal ends 108 of the clip arms 104.

In an embodiment, a pin 116 extends through the proximal end 108 in a transverse direction of each of the clip arms 104 via an opening 118 extending through each of the clip arms 104. As will be described in further detail below, the distal end 114 of the control member 112 releasably engages the pin 116 and the proximal ends 108 of the clip arms 104 so that, while attached to the pin 116, movement of the control member 112 proximally and distally moves the clip arms 104 proximally and distally relative to the capsule 106. The distal end of the control member, when coupled to the pin 116 also constrains the proximal ends 108 of the clip aims 104 to prevent the locking of the clip arms 104 in the capsule 106 until it is desired to lock the clip 102 in place on target tissue. The clip 102 is releasably coupled to a proximal portion 120 of the device 100 facilitating insertion of the clipping device 100 to a target site.

The proximal portion 120 includes an elongate member housing the control member 112 and connects the clip 102 to a handle and/or actuators which, during use, remain outside the body accessible to a user to permit the user to control movement of the device 100 between the open and closed configurations and to deploy the clip 102 over target tissue. The proximal portion 120 may include, for example, a flexible shaft 121 extending from a proximal end connected to a handle member (not shown) operable by a user external to a patient, including controls for moving and deploying the device 100, to a distal end 122 releasably coupled to a proximal end 124 of the capsule 106 via, for example, a bushing 126. The control member 112 extends through the flexible shaft 121 from a proximal end connected to a portion of the handle member to the distal end 114 connected to the clip arms 104.

The capsule 106 extends from the proximal end 124 to a distal end 128 and includes a channel 130 extending therethrough. In one embodiment, the proximal end 124 is configured to be releasably coupled to the bushing 126 via tabs 132 that are, for example, crimped radially inward to engage a corresponding portion of the bushing 126 at the distal end 122 of the flexible shaft 121. Although not shown, the distal end 128 may include inwardly bent tabs extending across an opening of the channel 120 to prevent the proximal ends 108 of the clip arms 104 from being distally therepast when the clip 102 is moved toward the open configuration. The capsule 106 also includes locking features formed in the capsule wall such as, for example, locking windows 134 that extend laterally through the capsule wall for engaging locking tabs 136 of the clip aims 104, as will be described in further detail below.

Each of the clip arms 104 extends from the proximal end 108 to the distal end 110. As described above, proximal portions of the clip anus 104 are slidably received within the channel 130 of the capsule 106. Specifically, the proximal end 108 of each of the clip arms 104 is slidably received within the channel 130 allowing the clip 102 to be moved between the open and closed configurations via manipulation of the control member 112. In one embodiment, the clip arms 104 are biased toward the open configuration so that, when drawn proximally into the capsule 106, the clip arms 104 are constrained by the wall of the capsule in the closed position with the distal ends 110 adjacent one another. When the clip arms 104 are moved distally to extend further out of the capsule 106, the clip arms 104 are freed from the constraint of the capsule 106 and to revert to the open configuration under their natural bias. Those skilled in the art will understand that any number of other mechanisms for opening and closing the clip aims may be employed.

The clip arms 104 of this embodiment also include engaging features 138 extending therefrom and configured to engage a portion of the capsule 106 so that, when the engaging features 138 engage the capsule 106, the clip arms 104 are prevented from being moved further proximally relative to the capsule 106. In one embodiment, the engaging features 138 extend laterally outward from a portion of the clip arms 104 so that, when the clip arms 104 are drawn proximally relative to the capsule 106, the engaging features 138 abut a portion of a distal face 129 of the capsule 106. The engaging features 138 are positioned along the clip aims 104 so that, at the point where the engaging features 138 have engaged the capsule 106, the clip arms 104 have been drawn sufficiently proximally into the capsule 106 to draw the clip arms 104 together into the closed configuration. In one example, the engaging features 138 are configured as wings extending laterally from longitudinal edges of the clip arms 104.

Proximal ends 108 of the clip arms 104 also include locking tabs 136 extending therefrom. The proximal ends 108, in an embodiment, are biased outward, radially away from a centerline of the capsule 106, but are restrained and prevented from engaging the wall of the capsule 106 while the distal end 114 of the control member 112 remains coupled to the clip 112. When the clip 102 is deployed, the control member 112 is released from the clip 102 and the locking tabs 136 are freed to spring outward to engage the locking windows 134 locking the clip arms 104 in the closed configuration over target tissue. The proximal ends 108 of the clip arms 104 also include the openings 118 permitting the pin 116 to extend through each of the clip arms 104 holding the clip arms 104 in a desired alignment relative to one another. In one embodiment, a length of the pin 116 in this embodiment substantially corresponds to a width (e.g., diameter) of the capsule 106 so that, as the clip arms 104 are moved longitudinally relative to the capsule 106, the pin 116 slides along an inner surface of the capsule 106.

The distal end 114 of the control member 112 is releasably coupled to the proximal ends 108 of the clip arms 104 holding the proximal ends 108 at a radially compressed position separated from the inner surface of the capsule 106 preventing the locking tabs 136 from engaging the locking windows 134 until the control member 112 is separated from the clip arms 104. As will be described in more detail below, the distal end 114 is sized and shaped to disengage the capsule 106 from the bushing 126 during deployment of the clip 102. In a pre-deployed configuration, as shown in FIG. 1, the distal end 114 releasably engages the pin 116 so that longitudinal movement of the control member 112 proximally and distally relative to the capsule 106 leads to a corresponding movement of the clip arms 104 relative to the capsule 106.

In one embodiment, the distal end 114 includes first and second jaws 140, 142 and first and second holding jaws 144, 146 for engaging the clip arms 104 and the pin 116. In particular, the first and second spacing jaws 140, 142 extend between the proximal ends 108 of the clip aims 104 (with interior surfaces of the clip arms 104 that face a central axis of the capsule 106 engaging radially outer surfaces of the jaws 140, 142). The first spacing jaw 140 extends along a first side of the pin 116 while the second spacing jaw 142 extends along a second side of the pin 116 substantially opposing the first side. The first and second spacing jaws 140, 142 extend between the clip arms 104 to hold the proximal ends 108 away from one another, to act as a positive stop on the distal end 128 of the capsule 106 when the clip 102 is in the open configuration, and as will be described in further detail below, to facilitate release of the capsule 106 from the proximal portion 120 during deployment.

Each of the first and second holding jaws 144, 146 extends over an exterior surface of the proximal end 108 of a corresponding one of the clip arms 104 to constrain the proximal ends 108 of the clip arms 104 and prevent the clip arms 104 from lockingly engaging the capsule 106 until the clip is deployed. In particular, the first holding jaws 144 extends along a surface of a first one of the clip arms 104 facing away from the centerline of the capsule 106 and the second holding jaw 146 extends along a surface of a second one of the clip arms 104 facing away from a centerline of the capsule 106. Each of the first and second holding jaws 144, 146 includes a pair of fingers 150 extending around opposing sides of the pin 116 with distal ends 152 of the fingers 150 curving around a distal surface of the pin 116 to grip the pin 116 until the jaws 140, 142, 144 and 146 are separated from the clip 102 and the clip 102 is deployed.

It will be understood by those of skill in the art that, in a further embodiment, distal ends 148 of the first and second spacing jaws 140, 142 may also curve toward one another to wrap about at least a portion of the distal surface of the pin 116 to provide an additional holding/gripping force of the pin 116 until it is desired to deploy the clip 102. Alternatively, according to another embodiment, the distal ends 148 of the first and second spacing jaws 140, 142 may be curved to grip the pin 116 while the fingers 150 of the first and second holding jaws 144, 146 merely extend along opposing sides of the pin 116 to constrain the proximal ends 108 of the clip arm 104 to prevent the clip arms 104 from lockingly engaging the capsule 106 until deployment.

As described above, the distal end 114 of the control member 112 is coupled to the pin 116 and the proximal ends 108 of the clip arms 104 so that the clip 102 may be moved between the open and closed configurations via movement of the control member 112. When the clip arms 104 are drawn proximally into the capsule 106 until the engaging features 138 engage the capsule 106 preventing further proximal movement of the clip arms 104 relative to the capsule 106, increased proximally directed force exerted on the control member 112, tension applied to the control member 112 increases until the fingers 150 of the first and second holding jaws 144, 146 are spread away from one another to release the pin 116 from the control member 112 freeing the proximal ends 108 of the clip arms 104 to spring outward until the locking tabs 136 engage the locking windows of the capsule 106 locking the clip 102 in the closed configuration.

After the control member 112 disengages from the pin 116 and the proximal ends 108 of the clip arms 102, the user continues to draw the control member 112 proximally until the distal end 114 is received in the proximal end 124 of the capsule 106. The distal portion 114 is sized and shaped so that, as it moves between the inwardly crimped tabs 132, the tabs 132 are forced radially outward disengaging the capsule 106 from the bushing 126 and separating the clip 102 from the proximal portion 120 of the device 100 so that the device 100 may be withdrawn from the body while the clip 102 remains in place clipped over the target tissue.

In one embodiment, exterior surfaces 154 of the first and second spacing jaws 140, 142 extend radially away from a centerline of the capsule 106 by a distance selected so that the jaws 140 and 142 abut the crimped tabs 132 and push the tabs 132 radially outward as the distal end 114 of the control member 112 moves proximally therepast. In this embodiment, a distance between exterior surfaces 154 of the first and second portions 140, 142 substantially corresponds to a width (e.g., diameter) of the channel 130 of the capsule 106 distal of the inwardly crimped tabs 132. As shown in FIG. 2, an interior channel of the bushing 126 is sized and shaped to receive the distal end 114 of the control member 112 therein after the clip 102 has been deployed. In this embodiment no portion of the control member 112 contributes to a length of the deployed clip 102, as shown in FIG. 3, and all portions of the control member 112 are removed from the body along with the proximal portion 120 of the clipping device 100 and without shedding any parts within the body.

According to an exemplary method utilizing the clipping device 100, the clip 102 is inserted through, for example, a working channel of an endoscope to a target site within a body while the handle member remains exterior to the body. The clip 102 is inserted through the working channel in the closed configuration. Once the clip 102 has reached the target site, the clip arms 104 are extended distally from the capsule 106 so that the clip arms 104 move under their natural bias toward the open configuration so that target tissue may be received between the clip arms 104. The user may operate the control member 112 to move the clip 102 between the open and closed configurations as desired until a target portion of tissue is positioned between the clip arms 104. The user then draws the control member 112 proximally (or advances the proximal portion 120 distally over the control member 112) so that, as more of the clip arms 104 are received into the capsule 106, the clip arms 104 are drawn toward one another to grip the target tissue between the distal ends 110 of the clip arms 104.

When the user is satisfied that the clip 102 is in position gripping the target tissue as desired, the user applies increasing proximally directed force to the control member 112 after the engaging features 138 have engaged the capsule 106, as described above, until the distal ends 152 of the fingers 150 of the holding jaws 144, 146, separate from one another releasing the pin 116. As the pin 116 is released, the distal end 114 of the control member 112 also disengages from the proximal ends 108 of the clip arms 104 freeing the proximal ends 108 to spring outward away from the centerline of the capsule 106 until the locking tabs 136 engage the locking windows 134 of the capsule 106 locking the clip 102 in the closed configuration. The user then draws the control member 112 further proximally relative to the capsule 106 until the distal end 114 engages the tabs 132 pushing them outward to disengage the capsule 106 from the bushing 126 and freeing the clip 102 that is coupled to the target tissue. The control member 112 may then be withdrawn proximally until the distal end 114 is received within the bushing 126 so that the proximal portion 120 with the entire the control member 112 received therein, may be removed from the body.

Figure 4:
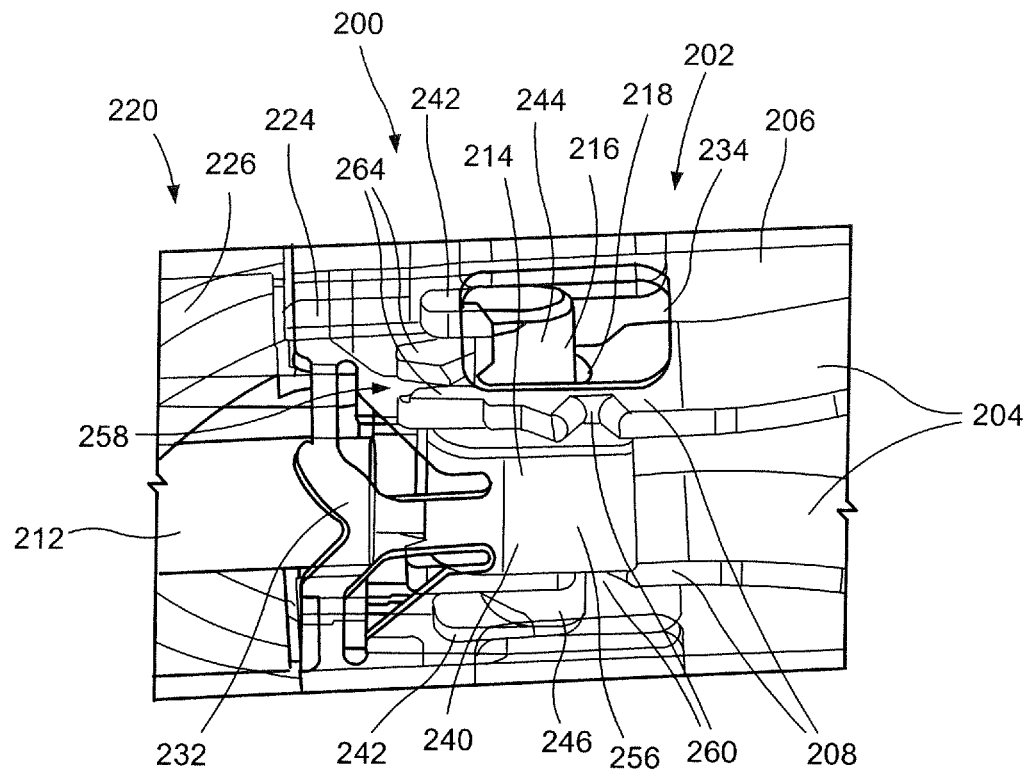
FIG. 4 shows a perspective view of a portion a clipping device according to a second exemplary embodiment of the present disclosure.
Figure 5:
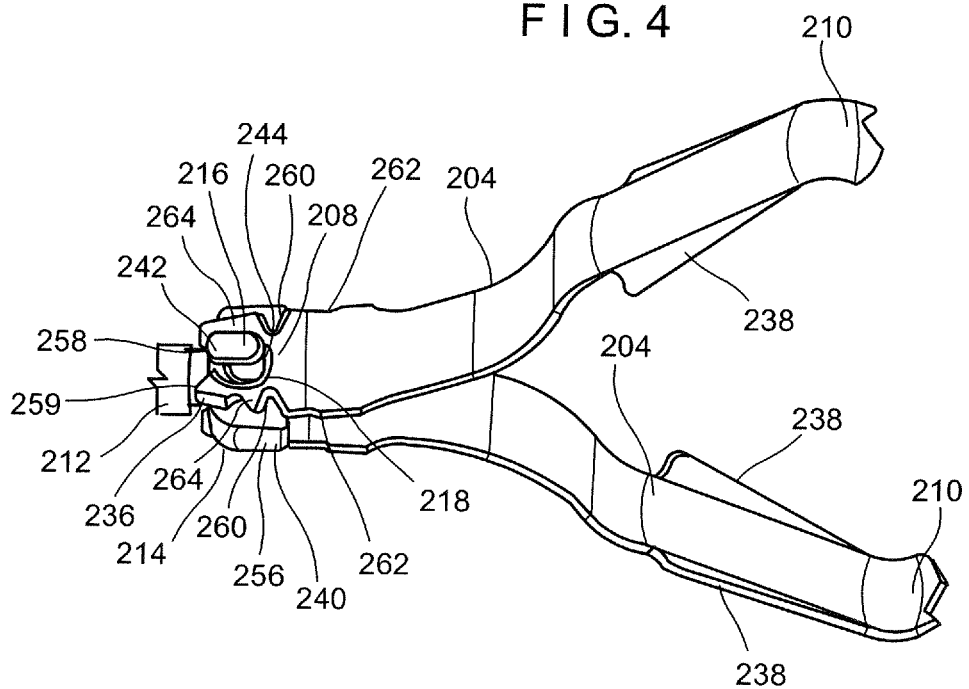
FIG. 5 shows a perspective view of clip arms and a control member of the clipping device of FIG. 3.

A clipping device 200 according to another exemplary embodiment, as shown in FIGS. 4-5, is substantially similar to the clipping device 100 described above and comprises a clip 202 including a pair of clip arms 204, proximal ends 208 of which are slidably received within a capsule 206 so that the clip 202 may move between an open configuration, in which distal ends 210 of the clip arms 204 are separated from one another, and a closed configuration, in which distal ends 210 are drawn toward one another. The clip aims 204 are moved between the open and the closed configurations via a control member 212 as described above and the control member 212 includes a distal end 214 configured to be directly coupled to the proximal ends 208 of the clip arms 204. The capsule 206, the clip arms 204 and a proximal portion 220 of the clipping device 200 to which the capsule 206 is releasably coupled are substantially similar to the corresponding elements of the device 100 described above. A pin 216 received within openings 218 extending through the proximal ends 208 of the clip arms 204, in this embodiment is integrally foamed with control member 212, and defines a portion of the distal end 214 of the control member 212 so that, as will be described in further detail below, the pin 216 is drawn out of the openings 218 during deployment of the clip 202.

The control member 212 is substantially similar to the control member 112, extending through the proximal portion 220 from a proximal end connected to a portion of a handle member to the distal end 214, which is releasably coupled to the proximal ends 208 of the clip arms 204. The distal end 214, however, includes a middle portion 240 sized and shaped to be received between the proximal ends 208 of the clip arms 204 and to have a width substantially corresponding to a width (e.g., diameter) of the capsule 206. The pin 216 is defined via a first portion 244 extending laterally away from a first surface of the middle portion 240 to be received within the opening 218 of a first one of the clip arms 204 and a second portion 246 extending laterally away from a second surface of the middle portion 240 opposing the first surface of the middle portion 240 to be received within the opening 218 of a second one of the clip arms 204.

Each of the first and second portions 244, 246 also includes a longitudinally extending tab 242 configured to engage exterior surfaces of the clip arms 204—e.g., surfaces along the proximal portion 208 of the clip arms 204 facing away from a centerline of the capsule 206—to constrain the proximal ends 208 toward the centerline of the capsule 206, preventing locking tabs 236 extending from the proximal ends 208 from engaging locking windows 234 of the capsule 206 until the clip 202 is deployed.

The clip arms 204 are substantially similar to the clip aims 104, extending from proximal ends 208 to distal ends 210 and including openings 218 extending through the proximal ends 208 to receive the pin 216. As described above with respect to device 100, the pin 216 is received within the openings 218 and holds the clip arms 204 in a desired alignment relative to one another. Each of the clip arms 204, however, includes a longitudinal slot 258 extending proximally from the opening 218 to a proximal edge 259 of the clip arms 204 to define a pair of fingers 264 extending proximally from the opening 218 and separated via the slot 258. The slot 258 has a width smaller than a width of the opening 218 and the pin 216 received therein so that simply moving the clip arms 204 between the open and closed configurations via the control member 212 does not disengage the control member 212 from the clip arms 214. Each of the clip arms 204 also includes a relief 260 formed along longitudinal edges 262 of the clip arms 204 immediately distal of the opening 218 so that, when a predetermined proximal force is exerted on the distal end 214 relative to the clip arms 204, the reliefs 260 allow the pair of fingers 264 to flex away from one another releasing the pin 216 from the control member 212.

The clipping device 200 may be used in a manner substantially similar to the clipping device 100. In particular, upon insertion to a target site within a body, the clip 202 may be moved between the open and closed configurations until a target portion of tissue is received between the distal ends 210 of the clip arms 204, as desired. Once the target tissue has been gripped as desired, the control member 212 is drawn proximally relative to the capsule 206 until engaging features 238 of the clip arms 208 engage the capsule 206 preventing further proximal motion of the clip arms 204 relative to the capsule 206. When the user is ready to deploy the clip 202, the user applies further proximally directed force to the control member 212 until the force applied by the pin 216 against the fingers 264 causes the fingers 264 to flex away from one permitting the pin 216 to move proximally through the widened slot 258 releasing the clip arms 204 from the control member 212 and freeing the proximal ends 208 of the clip aims 204 spring outward until the locking tabs 236 engage locking windows 234 to lock the clip 202 in the closed configuration.

The user then draws the control member 212 further proximally until the distal end 214 is drawn through the proximal end 224 of the capsule 206 forcing an exterior surface 256 of the middle portion 240 into engagement with the crimped tabs 232 forcing the tabs 232 radially outward, out of engagement with, for example, a bushing 226 of the proximal portion 220 and separating the clip 202 from the proximal portion 220 of the device 200. The distal end 214 is drawn proximally into the bushing 226 so that the proximal portion 220, and the control member 212, may be removed from the body. Similarly to the device 100, the control member 212 and the proximal portion 220 of the device 200 may be removed from the body without shedding any parts therewithin.

Figure 6:
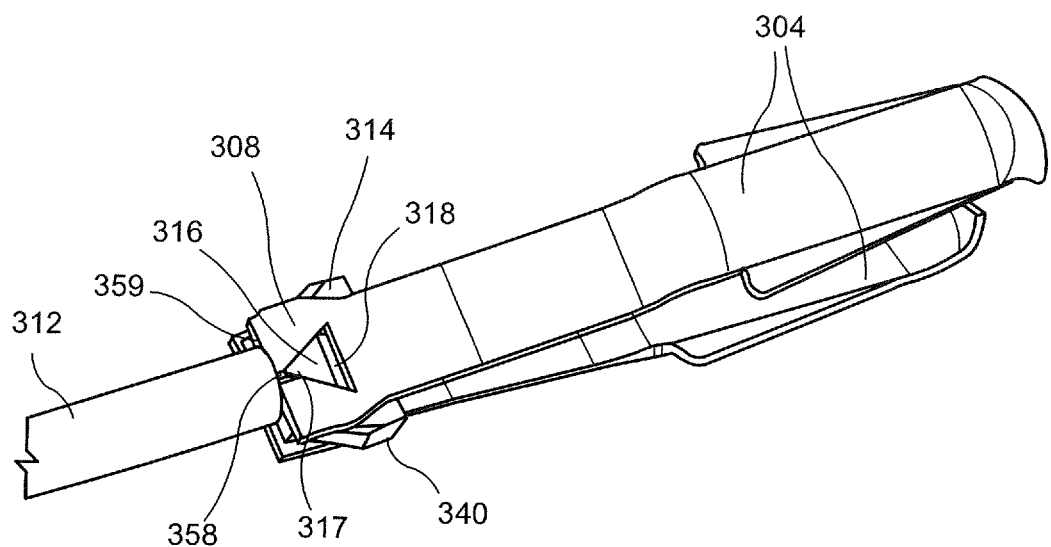
FIG. 6 shows a perspective view of clip arms and a control member according to a third exemplary embodiment of the present disclosure.
Figure 7:
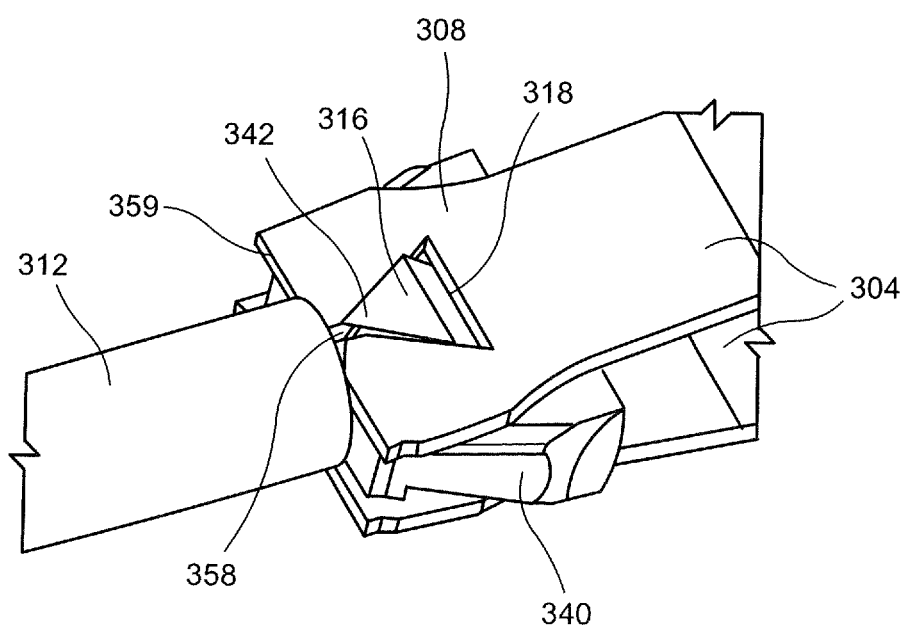
FIG. 7 shows an enlarged perspective view of the clip arms and the control member of FIG. 5.

Although the clip arms 204 are shown and described as including the slot 258 through which first and second portions 244, 246 of the pin 216 may pass to release the clip arms 204 from the control member 212, it will be understood by those of skill in the art that a pin 216 integrally formed with a remaining portion of the control member 212 may be released from the clip arms 204 to lock and deploy the clip 202 using other deployment mechanisms. For example, according to an alternate embodiment, as shown in FIGS. 6-7, clip arms 304 releasably engages a control member 312 via a distal end 314 thereof that includes a middle portion 340 received between proximal ends 308 of the clip arms 304. A pin 316 extending from opposing surfaces of the middle portion 340 is received within openings 318 along proximal ends 308 of the clip arms 304.

Similarly to the device 200 described above, the pin 316 couples the clip to the control member, maintains a desired alignment between the clip arms 304 and also constrains the proximal ends 308 at a radially inward unlocked configuration. The middle portion 340 is sized and shaped to disengage the capsule from the proximal portion during deployment by, for example, moving inwardly crimped tabs of the capsule outward when the distal end 314 is moved proximally therepast. Rather than a slot extending proximally from the openings 318 of the clip arms 304 to release the pin 316 during deployment, however, the proximal ends 308 are configured to be broken and split when a predetermined proximal force is exerted thereon via the pin 316.

In one embodiment, each of the clip arms 304 includes a notch 358 extending along an exterior surface of the clip wins 304 from the openings 318 to proximal edges 359 thereof. The notch 358 forms a weakened location that is configured to split when a predetermined force is exerted thereon via the pin 316. Although the pin 316 and the openings 318 of the clip arms 304 in which the pin 316 is received may have any of a variety of shapes, in one example, the pin 316 has a substantially triangular cross-section, tapering toward a proximal end 317 thereof and defining cutting edges for cutting and/or splitting the notch 358 as the pin 316 is moved proximally thereagainst. Similarly to the pin 216, ends of the pin 316 may include longitudinally extending tabs or overhangs 342 for holding the proximal ends 308 in the unlocked configuration until the pin 316 is drawn out of engagement with the proximal ends 308. The longitudinally extending tabs 342 in this embodiment are substantially triangular. It will be understood by those of skill in the art, however, that the longitudinally extending tabs 342 may have any of a variety of shapes so long as the longitudinally extending tabs 342 engage exterior surfaces of the proximal ends 308 of the clip arms 304—e.g., surfaces along the proximal portion 308 of the clip arms 304 facing away from the middle portion 340—to hold the proximal ends 308 in the unlocked configuration.

It will be understood by those of skill in the art that a strength of the deployment mechanism shown and described with respect to FIGS. 6 and 7 may be optimized for different applications based on a depth of the notch 358, a cutting edge angle of the pin 316 and a thickness of a material of the proximal ends 308 of the clip arms 304. Different configurations may be used to adjust a predetermined proximal force required for deployment to meet deployment requirements for multiple applications. It will also be understood by those of skill in the art that a clipping device including the deployment mechanism shown and described with respect to FIGS. 6 and 7 may be used in a manner substantially similar to the clipping device 200, as described above.

It will be apparent to those skilled in the art that various modifications may be made in the present disclosure, without departing from the scope of the disclosure.

What is claimed is:

1. A clipping device, comprising:
   a clip including a capsule extending longitudinally from a proximal end to a distal end and including a channel extending therethrough, and a pair of clip arms, proximal ends of which are slidably received within the channel to move the clip arms between an open configuration, in which distal ends thereof are separated from one another, and a closed configuration, in which the distal ends of the clip arms are drawn toward one another, the clip arms being aligned relative to one another via a pin received within openings extending through proximal ends of the clip arms;
   a proximal portion configured for insertion of the clip through a working channel of an endoscope, the proximal portion including a flexible shaft extending from a proximal end to a distal end including a bushing releasably coupled to the capsule; and
   a control member extending longitudinally through the flexible shaft from a proximal end to a distal end releasably coupled to the proximal ends of the clip arms to move the clip aims between the open and closed configurations, the distal end of the control member including a pair of holding jaws, each of which include a pair of fingers extending about the pin along opposing sides thereof to grip the pin therebetween.

2. The device of claim 1, wherein the proximal end of the capsule includes tabs biased radially inward to engage a corresponding structure of the bushing.

3. The device of claim 2, wherein the distal end of the control member includes a pair of spacing jaws configured to extend between the proximal ends of the clip arms along opposing sides of the pin, the pair of spacing jaws sized and shaped so the pair of spacing jaws move the tabs radially outward as the distal end of the control member is moved proximally past the proximal end of the capsule to deploy the clip from the proximal portion of the device.

4. The device of claim 1, wherein the proximal ends of the clip arms are biased radially outward.

5. The device of claim 4, wherein the pair of holding jaws extend over an exterior surface along a proximal end of a corresponding one of the clip arms to constrain the clip aims toward an unlocked configuration in which locking structures at the proximal ends of the clip arms are prevented from engaging corresponding locking features of the capsule.

6. The device of claim 5, wherein the locking structures include locking tabs extending from proximal ends of the clip arms and the locking features of the capsule including locking windows extending laterally through a wall thereof so that, when the proximal ends of the clip are released from the distal end of the control member, the locking tabs are received within the locking windows to lock the clip in the closed configuration.

7. The device of claim 1, wherein the clip arms are biased toward the open configuration so that the clip arms are constrained toward the closed configuration via an interior surface of the capsule and revert to the biased open configuration when the clip arms are moved distally out relative to the capsule.

8. The device of claim 1, wherein the clip arms include engaging features configured to engage portion of the capsule such that, when the engaging features engage the capsule, the clip arms are prevented from moving further proximally relative to capsule and a predetermined force is exerted on the distal end of the control member.

9. A clipping device, comprising:
   a clip including a capsule extending longitudinally from a proximal end to a distal end and including a channel extending therethrough, and a pair of clip arms, proximal ends of which are slidably received within the channel to move the clip arms between an open configuration, in which distal ends thereof are separated from one another, and a closed configuration, in which the distal ends of the clip arms are drawn toward one another;
   a proximal portion configured for insertion of the clip through a working channel of an endoscope, the proximal portion including a flexible shaft extending from a proximal end to a distal end including a bushing releasably coupled to the capsule; and
   a control member extending through the flexible shaft from a proximal end to a distal end releasably coupled to the proximal ends of the clip aims to move the clip arms between the open and the closed configurations, the distal end including a middle portion received between the proximal ends of the clip anus, a first portion of a pin and a second portion of the pin extending away from opposing surfaces of the middle portion to be received in openings extending through proximal ends of the clip arms to maintain an alignment of the clip alms relative to one another, the first and second portions being pulled proximally out of the openings of the clip arms and past a proximal edge thereof when a predetermined force is exerted on the clip arms via the distal end.

10. The clipping device of claim 9, wherein each of the first and second portions include an overhang extending therefrom to extend over a portion of an exterior surface along the proximal end of a corresponding one of the clip arms to constrain outwardly biased proximal ends of the clip arms toward an unlocked configuration, in which proximal ends are constrained toward a middle portion received therebetween so that locking structures along the proximal ends of the clip arms are prevented from engaging corresponding locking features of the capsule.

11. The device of claim 10, wherein each of the clip arms include a slot extending proximally from the opening to a proximal edge thereof to define two fingers which flex apart from one another to release the pin therefrom, when the predetermined force is exerted on thereon.

12. The device of claim 11, wherein each of the clip arms include reliefs along longitudinal edges of the clip arm immediately distal of the opening to facilitate flexing of the two fingers away from one another.

13. The device of claim 10, wherein each of the clip arms include a notch extending along a surface thereof from the opening to a proximal edge thereof so that, when the predetermined force is exerted thereon via the pin, the clips separate along the notch to release the pin from the openings.

14. The device of claim 13, wherein the first and second portions of the pin taper toward a proximal end thereof to split each of the clip arms along the notch.

15. The device of claim 10, wherein the proximal end of the capsule includes tabs biased radially inward to engage a corresponding structure of the bushing, the middle portion being sized and shaped to move the tabs radially outward as the distal end of the control member is moved proximally past the proximal end of the capsule to deploy the clip from the proximal portion of the device.

16. A method for treating a target tissue, comprising:

inserting a clip device through a working channel of an endoscope to a target site within a body until a clip of the clip device extends distally past a distal end of the working channel, the clip device including a capsule and a pair of clip arms slidably received therein, the pair of clip arms aligned relative to one another via a pin extending through openings extending through proximal ends of the clip aims;

moving the clip device between an open configuration, in which distal ends of the clip arms are separated from one another, and a closed configuration, in which the distal ends of the clip arms are drawn toward one another, via a control wire coupled to the clip anus, until a target tissue is received between the distal ends as desired, a distal end of the control wire coupled to proximal ends of the clip arms via first and second holding jaws, each of which include a pair of fingers extending about the pin along opposing sides thereof to grip the pin therebetween;

drawing the clip arms proximally into the capsule to move the clip toward the closed configuration to grip the target tissue between the clip arms; and deploying the clip from a proximal portion of the clip device by drawing a control member proximally relative to the capsule until a predetermined force is exerted on the distal end of the control wire to spread the fingers apart from one another and release the pin from therebetween.

17. The method of claim 16, wherein the distal end of the control wire includes a pair of spacing jaws configured to extend between the proximal ends of the clip arms along opposing sides of the pins.

18. The method of claim 17, wherein deploying the clip includes moving the distal end of the control member proximally past a proximal end of the capsule connected to a bushing so that the pair of spacing jaws engage radially inwardly crimped tabs of the capsule to move the tabs radially outward out of engagement with the proximal portion of the clip device.

19. The method of claim 18, wherein each of the first and second holding jaws extend along an exterior surface of a corresponding one of the clip arms to constrain the proximal ends of the clip arms toward an unlocked configuration, in which proximal ends are locking structures along the proximal ends of the clip anus are prevented from engaging corresponding locking features of the capsule.

20. The method of claim 16, wherein proximal ends of the clip arms are biased toward a radially outward configuration.

* * * * *